United States Patent
Ojha et al.

(10) Patent No.: US 8,724,875 B2
(45) Date of Patent: May 13, 2014

(54) ATTENUATION CORRECTION FOR PET OR SPECT NUCLEAR IMAGING SYSTEMS USING MAGNETIC RESONANCE SPECTROSCOPIC IMAGE DATA

(75) Inventors: Navdeep Ojha, Mayfield Village, OH (US); Michael Morich, Mentor, OH (US)

(73) Assignee: Koninklijke Philips N.V., Eindhoven (NL)

( * ) Notice: Subject to any disclaimer, the term of this patent is extended or adjusted under 35 U.S.C. 154(b) by 502 days.

(21) Appl. No.: 13/055,768

(22) PCT Filed: Jul. 22, 2009

(86) PCT No.: PCT/IB2009/053195
§ 371 (c)(1),
(2), (4) Date: Jan. 25, 2011

(87) PCT Pub. No.: WO2010/018478
PCT Pub. Date: Feb. 18, 2010

(65) Prior Publication Data
US 2011/0123083 A1    May 26, 2011

Related U.S. Application Data

(60) Provisional application No. 61/089,176, filed on Aug. 15, 2008, provisional application No. 61/112,205, filed on Nov. 7, 2008.

(51) Int. Cl.
*G06K 9/00* (2006.01)
*G01R 33/46* (2006.01)
*G01R 33/48* (2006.01)
*G01R 33/485* (2006.01)
*G01N 24/08* (2006.01)

(52) U.S. Cl.
CPC .............. *G01R 33/46* (2013.01); *G01R 33/481* (2013.01); *G01R 33/485* (2013.01); *G01N 24/08* (2013.01)
USPC ....................................... 382/131

(58) Field of Classification Search
USPC ............................ 382/128–132; 600/407, 458
See application file for complete search history.

(56) References Cited

U.S. PATENT DOCUMENTS

| 6,429,434 B1 | 8/2002 | Watson et al. |
| 2004/0101183 A1* | 5/2004 | Mullick et al. ................ 382/131 |

(Continued)

FOREIGN PATENT DOCUMENTS

WO    2008064319 A2    5/2008

OTHER PUBLICATIONS

Zaidi et al., ("Magnetic resonance imaging-guided attenuation and scatter correction in three-dimensional brain positron emission tomography", Medical physics, vol. 30, No. 5, May 1, 2003, pp. 937-948).*

(Continued)

*Primary Examiner* — Amara Abdi

(57) ABSTRACT

When correcting for attenuation in a positron emission tomography (PET) image, a magnetic resonance (MR) image (24) of a subject is generated with spectroscopic data (38) describing the chemical composition of one or more of the voxels in the MR image. A table lookup is performed to identify a tissue type for each voxel based on the MR image data and spectral composition data, and an attenuation value is assigned to each voxel based on its tissue type to generate an MR attenuation correction (MRAC) map (30). The MRAC map (30) is used during reconstruction of the nuclear image (37) to correct for attenuation therein. Additionally, attenuation due to MR coils and other accessories that remain in a nuclear imager field of view during a combined MR/nuclear scan is corrected using pre-generated attenuation correction maps that are applied to a nuclear image after executing an MR scan to identify anatomical landmarks, which are used to align the pre-generated attenuation correction maps to the patient.

23 Claims, 6 Drawing Sheets

(56) References Cited

U.S. PATENT DOCUMENTS

2007/0055161 A1* 3/2007 Garg et al. .................... 600/458
2009/0122060 A1* 5/2009 Porat et al. .................... 345/424
2010/0284593 A1* 11/2010 Delsanto et al. ............. 382/130

OTHER PUBLICATIONS

Chu et al., (Regional cerebral blood flow and magnetic resonance spectroscopic imaging findings in diaschisis from stroke, vol. 33, No. 5, Jan. 1, 2002, pp. 1243-1248).*

Montandon et al (Strategies for attenuation compensation in neurological PET studies, NeuroImage, vol. 34, No. 2, Dec. 2, 2006, pp. 518-541).*

"Alternative methods for attenuation correction for PET images in MR-PET scanners" Kops, E.R.; Herzog, H.; Nuclear Science Symposium Conference Record, 2007. NSS apos;07. IEEE vol. 6, Issue, Oct. 26, 2007-Nov. 3, 2007 pp. 4327-4330.

"MRI Based Attenuation Correction for Brain PET Images" Elena Rota Kops, Peng Qin, Mattea Muller-Veggian and Hans Herzog, Advances in Medical Engineering, Springer Berlin Heidelberg, 2007, vol. 114, pp. 93-97.

Chu, W., et al.; Regional Cerebral Blood Flow and Magnetic Resonance Spectroscopic Imaging Findings in Diaschisis from Stroke; 2002; Stroke; 33(5)1243-1248.

Hetherington, H. P., et al.; Evaluation of Cerebral Gray and White Matter Metabolite Differences by Spectroscopic Imaging at 4.1T; 1994; MRM; 32(5)565-571.

Laudadio, T., et al.; Tissue Segmentation and Classification of MRSI Data Using Canonical Correlation Analysis; 2005; MRM; 54:1519-1529.

Zaidi, H., et al.; Strategies for attenuation compensation in neurological PET studies; 2007; NeuroImage; 34:518-541.

Zaidi, H., et al.; Magnetic resonance image guided attenuation and scatter corrections in three-dimensional brain positron emission tomography; 2003; Med. Phys.; 30(5)937-948.

* cited by examiner

ATTENUATION CORRECTION FOR PET OR SPECT NUCLEAR IMAGING SYSTEMS USING MAGNETIC RESONANCE SPECTROSCOPIC IMAGE DATA

CROSS REFERENCE TO RELATED APPLICATIONS

This application claims the benefit of U.S. provisional application Ser. No. 61/089,176 filed Aug. 15, 2008 and U.S. provisional application Ser. No. 61/112,205 filed Nov. 7, 2008, both of which are incorporated herein by reference.

The present disclosure finds particular application in patient imaging systems, particularly involving patient imaging devices such as single photon emission computed tomography (SPECT), positron emission tomography (PET) scanners, and the like. However, it will be appreciated that the described technique may also find application in spectroscopy systems, other nuclear imaging scenarios, other imaging techniques, and the like.

Unlike computed tomography (CT) images in which the pixel value is related to radiation attenuating properties of a pixel or voxel, magnetic resonance (MR) images are based on resonance signals from resonating dipoles, typically a hydrogen dipole. Others have proposed using MR image data to calculate attenuation factors by using MR image intensity to classify each voxel as either tissue or air. Still others have proposed using magnetic resonance properties of the tissue to separate the soft tissue from the bone such that each voxel was classified as one of soft tissue, bone, or air and given the attenuation factor assigned to that class.

In nuclear imaging, as the gamma rays (photons) travel through the body, there is attenuation of the total number of photons reaching the detectors. This leads to a decrease in the number of detected photons with path lengths that encounter tissues with high attenuation, which further causes poor quantification of "hot spots" inside the body and can cause clinical misdiagnosis.

Attenuation correction (AC) is a quantitative technique applied to nuclear images to correct for effects of photon attenuation. While nuclear imaging incorporates an emission image obtained from a radionuclide distributed within the subject's body, AC uses additional data of the patient's tissue photon-attenuation distribution to create a map of the body's attenuation effects. The attenuation information traditionally comes from a CT scanner or nuclear CT images (images reconstructed from transmission radiation by a nuclear scanner). This information is applied to the reconstruction of nuclear images which results in counteracting the attenuating effects of body. In PET-MR scanners, the traditional radiographic techniques for effectively providing AC of PET images are not available. The technique described here proposes a solution to AC problem using MR images.

In combined nuclear/MR imaging, local MR coils (e.g., breast coils, endorectal coils, etc.) from an MR scan are often left on or in a patient during a nuclear scan (e.g., PET or SPECT), and can cause attenuation in the nuclear image. Classical methods of addressing such attenuation involve fiducial markers to identify the location of the coils in the nuclear image and correct attenuation caused thereby. However, such methods involve modification of standard MR coils that otherwise should be useful for general MR imaging procedures. Modifications of coils are time consuming and labor-intensive and duplication of coil sets, one for MR-only and one for PET-MR is costly. Additionally, MR fiducials generate RF signals that can cause artifacts that can alias into the MR image.

The present application provides new and improved systems and methods for attenuation correction in multi-modal imaging systems, whereby MR image data is used to generate an MRAC with chemical shift information, and the MRAC is employed to generate an artifact-free attenuation map for correcting the PET image, which overcome the above-referenced problems and others.

In accordance with one aspect, an image correction system includes a memory that stores magnetic resonance (MR) spectroscopic image data acquired during an MR scan of a subject. The system further includes a processor that determines a spectrum for voxels selected from the MR spectroscopic image data, determines a tissue type for each voxel based on its spectrum, converts each tissue type into a photon attenuation value, and assembles the attenuation values for each voxel into an MR attenuation correction (MRAC) map. The system also includes a nuclear imaging reconstruction processor that reconstructs nuclear image data into attenuation corrected nuclear image data in accordance with the MRAC map.

In accordance with another aspect, a method of correcting attenuation in a nuclear image includes obtaining MR image data for one or more voxels in an MR image and spectroscopic data for at least one of the one or more voxels in the MR image, determining a chemical spectrum for each of the one or more voxels, and identifying a tissue type for each respective voxel as a function of a chemical composition of the voxel determined from the spectrum of the voxel. The method further includes performing a table lookup for attenuation values for respective tissue types, assigning an attenuation value to each voxel in the MR image as a function of the tissue type identified for the voxel, to generate an MR attenuation correction (MRAC) map, and reconstructing an attenuation-corrected nuclear image from acquired nuclear image data using the MRAC map.

In accordance with another aspect, a computer readable medium having stored thereon software for controlling one or more computers to correct for attenuation in a nuclear image, the software including instructions for obtaining MR image data for one or more voxels in an MR image and spectroscopic data for at least one of the one or more voxels in the MR image, and determining a chemical spectrum for each of the one or more voxels. The software further includes instructions for identifying a tissue type for each respective voxel as a function of a chemical composition of the voxel determined from the spectrum of the voxel, performing a table lookup for attenuation values for respective tissue types, and assigning an attenuation value to each voxel in the MR image as a function of the tissue type identified for the voxel, to generate an MR attenuation correction (MRAC) map. The software further includes instructions for reconstructing an attenuation-corrected nuclear image from acquired nuclear image data using the MRAC map.

According to another aspect an apparatus for correcting attenuation in a nuclear image using magnetic resonance (MR) image data and spectroscopic data includes means for generating MR image data for one or more voxels in an MR image and spectroscopic data for at least one of the one or more voxels in the MR image, means for determining a chemical spectrum for each of the one or more voxels, and means for identifying a tissue type for each respective voxel as a function of a chemical composition of the voxel determined from the spectrum of the voxel. The apparatus further includes means for performing a table lookup for attenuation values for respective tissue types, means for assigning an attenuation value to each voxel in the MR image as a function of the tissue type identified for the voxel, to generate an MR attenuation correction (MRAC) map, and means for reconstructing an attenuation-corrected nuclear image from acquired nuclear image data using the MRAC map.

According to yet another aspect, a method of correcting attenuation in a nuclear image includes obtaining MR image data for one or more voxels in an MR image and spectroscopic data for at least one of the one or more voxels in the MR image, and determining a chemical spectrum for each of the one or more voxels. The method further includes identifying a tissue type for each respective voxel as a function of a chemical composition of the voxel determined from the spectrum of the voxel, wherein the chemical composition of a voxel includes one or more of choline, creatinine, N-Acetyl Aspartate, and lipid, and wherein tissue type associated with each voxel is determined as a function of the specific chemical composition thereof. The method additionally includes performing a table lookup for attenuation values for respective tissue types, assigning an attenuation value to each voxel in the MR image as a function of the tissue type identified for the voxel, to generate an MR attenuation correction (MRAC) map, and reconstructing an attenuation-corrected nuclear image from acquired nuclear image data using the MRAC map.

According to another aspect, a method of correcting attenuation in a nuclear image using a pre-generated attenuation correction map includes performing an MR scan of the patient to generate an image of a region of interest in the patient, and identifying one or more anatomical landmarks in the image to which an attenuation-causing item has a fixed relative position. The method further includes aligning the attenuation map of the attenuation-causing item with the patient, acquiring nuclear image data from the patient, and reconstructing the nuclear image data using the aligned attenuation correction map.

According to yet another aspect, a method of correcting attenuation in a nuclear image using a pre-generated attenuation correction map includes performing a pilot MR scan of a patient using a system body coil for transmission and a single- or multi-channel local RF receive coil for reception, generating a spatially-resolved, low-resolution B1 map from acquired MR scan data, and inferring a position of the local receive RF coil relative to the patient from the B1 map. The method further includes acquiring nuclear scan data of a patient, and applying a pre-generated attenuation correction map when reconstructing a nuclear image from the acquired nuclear scan data to mitigate attenuation caused by the RF coil.

One advantage is that different types of soft tissue are differentiated.

Another advantage resides in correcting attenuation in a PET image using the differentiated soft tissue type information.

Another advantage resides in determining the physical relationship between MR coils and the patient for the purpose of correcting attenuation in a PET image acquired with the MR coils present.

Another advantage resides in the generation of additional diagnostic information from generating an attenuation map.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

Figure 1:
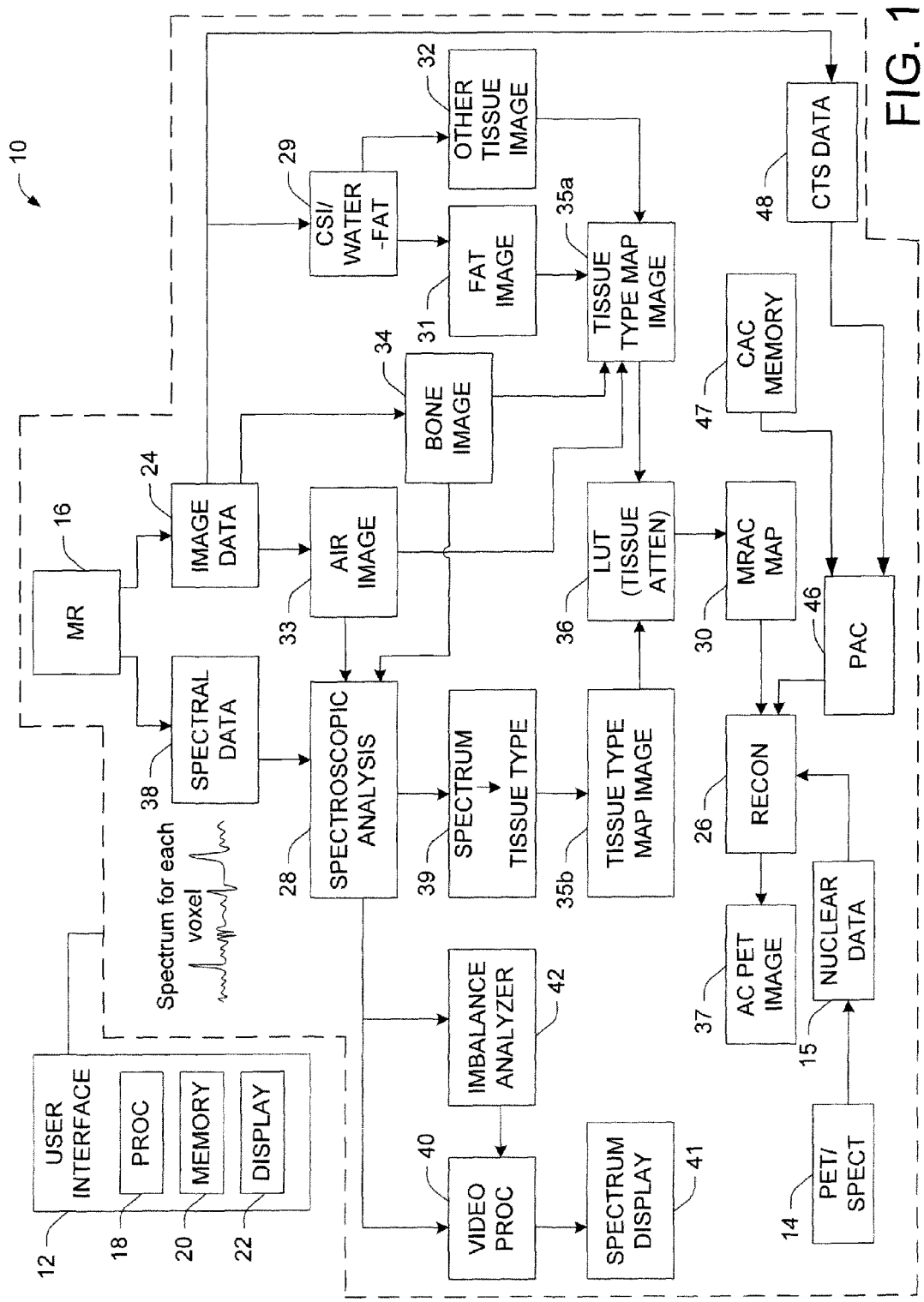
FIG. 1 illustrates a system that uses magnetic resonance to determine the attenuation values for PET imaging by differentiating among various types of soft tissue.

FIG. 1 illustrates a system 10 that uses magnetic resonance to determine the attenuation values for PET or other types of nuclear imaging by differentiating among various types of soft tissue, such as fat and muscle. A chemical shift imaging (CSI) and/or spectroscopic imaging technique, which are provided in a magnetic resonance imaging system, is used to determine the relative concentration of various preselected metabolites or tissue types. The relative concentrations of the metabolites in each voxel are indicative of the type of tissue represented by the voxel and can carry valuable diagnostic information. A matching algorithm or look up table can match the various metabolite concentrations and ratios to a corresponding tissue type, and match each tissue type to a corresponding attenuation factor.

The system 10 comprises a user interface 12 (e.g., a workstation or the like) that is coupled to each of a nuclear scanner 14 (e.g., a PET scanner, a SPECT scanner, etc.) that generates nuclear data 15 and an MR device 16. In one embodiment, the MR device 16 includes a quadrature body coil (not shown) for collecting MR signals from which a whole-body or regional image is generated. The user interface 12 comprises a processor 18, which is coupled to a memory 20, both of which are further coupled to a display 22. The memory 20 stores, and the processor generates, analyzes, and/or executes, image data 24 from the nuclear scanner 14 and/or the MR device 16, reconstruction algorithms and/or processor 26 for reconstructing nuclear and/or MR image representations from acquired scan data, spectroscopy algorithms 28 for generating voxel metabolite concentration information, chemical shift sequences and/or water-fat separation imaging sequences 29 for differentiating muscle tissue from fat or other lipids, attenuation correction map(s) 30 generated from MR data to compensate for attenuated nuclear data, PET correction algorithms for correcting PET data and/or images, etc. The processor generates a fatty tissue image 31 and an "other tissue" image 32 of non-fatty tissue from the chemical shift information generated by the chemical shift sequences 29. The block 29 could also be a water-fat separation imaging sequence. In this case an image is produced that is representative of the water concentration and an image is produced that is representative of the fat concentration using the Dixon technique or a spectral fat saturation and/or water saturation technique.

The processor 18 further analyzes the MR image data 24 to distinguish voxels associated with air and bone tissue. The processor generates air voxel image data 33 and bone voxel image data 34. It is to be appreciated and/or understood that some air voxels include tissue, for example the lungs, and some do not (e.g., the cavity of the bowel).

In one embodiment, the processor 18 employs information related to the distinguished voxel types (fatty tissue 31, non-fatty tissue 32, air 33, and bone 34) to generate a tissue type map or image 35a, and employs a look-up table (LUT) 36 to determine a mu-value (e.g., an attenuation value for 511 keV photons) for each tissue type, since different tissue types cause different levels of attenuation of nuclear scan data. Once each voxel has been assigned an attenuation value from the LUT, the processor generates the MR attenuation correction (MRAC) map 30. The reconstruction processor 26 receives the nuclear scan data 15 from the nuclear scanner 14, and applies the MRAC map 30 to correct for attenuation in the nuclear data 15 when generating an attenuation corrected nuclear image 38 (e.g., PET or SPECT).

In another embodiment, air and/or bone voxels identified in the MR image data 24 are analyzed using the spectroscopic analysis algorithms 28. Alternatively, one or both of the air and bone voxels are excluded from spectroscopic analysis to increase system speed and permit the system to focus resources on spectroscopic analysis of tissue voxels. The MR device 16 generates spectral data 38 for each voxel or a subset of voxels, in addition to the image data 24. The spectral data is analyzed by processor 18 using the spectroscopic analysis algorithm(s) 28, and a spectrum-to-tissue type conversion 39 is executed, which identifies voxels as a given tissue type based on their respective spectrums. The processor 18 uses the tissue type information to generate a tissue type map or image 35b, and accesses the LUT 36 to identify and/or assign an attenuation value for each voxel based on the voxel's tissue type. The processor generates the MRAC map 30 using the attenuation values determined from the LUT. The reconstruction processor 26 receives the nuclear scan data 15 from the nuclear scanner 14, and applies the MRAC map 30 to correct for attenuation in the nuclear data 15 when generating an attenuation corrected nuclear image 38 (e.g., PET or SPECT).

It will be appreciated that the described algorithms comprise computer-executable instructions that are persistently stored to the memory or other tangible storage medium, and recalled and executed by the processor, to carry out the various functions described herein.

In another embodiment, the processor 18 generates a whole body MRAC map from acquired MR data. When the nuclear scanner 14 is a PET scanner, the processor executes PET correction algorithm(s) to reconstruct an attenuation-corrected PET image representation that is free of artifacts. For instance, the processor 18 characterizes or segments an image volume (e.g., tissue or phantom) into different types of tissues such as by executing the spectroscopy algorithm(s) 28. The spectroscopy algorithm defines a 3D array of voxels and spectroscopically analyzes the MR signal from each voxel. The system 10 thus images tissue in the MR scanner 16 to generate spectroscopic data for each voxel which identifies a tissue type for each voxel that is input into the look up table to generate the MRAC map 30, which is used for correcting for photon attenuation during PET imaging. The spectrum for each voxel is analyzed to determine the metabolites present in each voxel. From the metabolites in each voxel, the predominant tissue type is determined to produce a tissue type map or image. The look up table 36 is pre-generated using known 511 keV photon attenuation values or the like, to cross-reference the tissue type information from each voxel with a corresponding attenuation value for each voxel to generate the 3D MRAC map 30 of attenuation values for the tissue. A weighted average of attenuation for one or more voxels may be used based upon the spectral characteristics. The resolution of the MRAC map is configurable and substantially equal to the resolution of the 3D spectroscopy voxel size. The MRAC map can be lower resolution than the reconstructed nuclear image. Alternatively, interpolation techniques can be employed to generate the MRAC map in higher resolution. In one embodiment, the MR data is analyzed to identify and automatically segment voxels corresponding to lungs, air pockets in the rest of body, bone, or other tissues or structures that can optionally be excluded from the spectroscopic analysis to increase system speed and/or reduce processing time.

The system 10 thus provides a quantitative software/hardware arrangement for multimodal PET-MR scanners where an MRI technique is used to generate the MRAC map of the whole or a portion of the body. In one embodiment, the software application and/or algorithms for generating the MRI data is a part of an acquisition computer (e.g., Windows-based or the like) of an MRI system. The algorithms for generating the MRAC map are run either on the same computer system as the MRI data acquisition algorithms or on another computer with access to the MRI-generated data.

According to another embodiment, the spectral data 38 is analyzed using the spectroscopic analysis algorithm(s) 28, and sent to a video processor 40 for processing and display on a spectrum display 41. Optionally, an imbalance analyzer 42 analyzes metabolite concentration information for respective voxels and generates metabolite imbalance information for the voxels, and the imbalance information is displayed with the spectral voxel data on the spectral display 41. The relative balance of metabolites provides valuable diagnostic information. For example, one use of PET imaging is for cardiac stress tests. The cardiac stress also causes an alteration in the metabolite balance. Thus, in addition to generating the attenuation correction value for each voxel, metabolite balance information is also provided and can be displayed.

In another embodiment, a preliminary T1-weighted or proton-density weighted magnetic resonance image with relatively low image contrast with respect to soft tissues is used to differentiate air or air-dominated tissue from all other tissue. This technique quickly identifies the voxels corresponding to air while conserving time and computational resources associated with the process of performing a spectroscopic analysis on air-dominated tissue voxels. Similarly, the preliminary image can be used to differentiate bone, implants, etc.

In another embodiment, a differentiation between fat and muscle is performed. By way of background, in magnetic resonance imaging, the hydrogen atoms in water and the hydrogen atoms in fat resonate at slightly different frequencies. Because position is encoded by frequency, this causes a chemical shift in which the fat tissue is shifted in the frequency encode direction. Numerous techniques have been developed for differentiating between fat and muscle, suppressing the signal from fat, suppressing the signal from water-dominated tissue, etc. These techniques can be utilized to differentiate between fat and other soft tissue in which the resonance signal is primarily from the hydrogen atoms in water.

For MR coils that are applied in a fixed location on or in the patient, such as a breast coil, knee coil, prostate coil, or a head coil, the coils are in a fixed location relative to the anatomy. Thus, from the MR-determined anatomical landmarks, the location of the coil relative to the anatomy can be inferred. This concept is also applicable to other types of coils and accessories that are in, or can be placed in, a relatively fixed location relative to the patient's anatomy, such as headphones, hand-held call buttons, and the like.

In combined PET-MR scanning (e.g., sequential, simultaneous, etc.), radio frequency (RF) surface coils are employed for high-resolution MR images. Clinical workflow often precludes removal of the RF coil(s) and/or accessories (headphones, nurse call device, etc) before starting a PET scan to minimize positioning disturbances of the subject. The RF coils thus often end up in the PET field of view and cause image quality degradation and/or attenuation artifacts. To address such coil attenuation, a photon attenuation correction (PAC) component 46 executes a software-based technique that calculates attenuation caused by certain surface coils and accessories automatically without the need for external fiducial markers and/or other such methods. A coil attenuation characteristics (CAC) memory 47 stores a description of the geometry, mounting location information, and coil attenuation correction characteristics on maps for each of a plurality of coil types, accessories, and/or patient body types (e.g., tall, short, obese, pediatric, etc.). The PAC looks to a characteristic tissue structure (CTS) data memory 48 that determines the location of characteristic anatomical structures near which the coil is mounted or positioned. Based on the coil geometry and mounting location information from the CAC memory 47, the PAC derives a transform for transforming or moving the stored coil attenuation map into alignment with the subject and the MR attenuation map 30. The aligned coil and MR attenuation maps can be combined or applied serially to correct the PET data. The coil attenuation maps are used for coils or accessories that may not have a fixed position relative to a patient support or table, but that have a fixed position relative to the patient. The PAC component 46 and technique are described in greater detail with regard to FIGS. 5-6.

Figure 2:
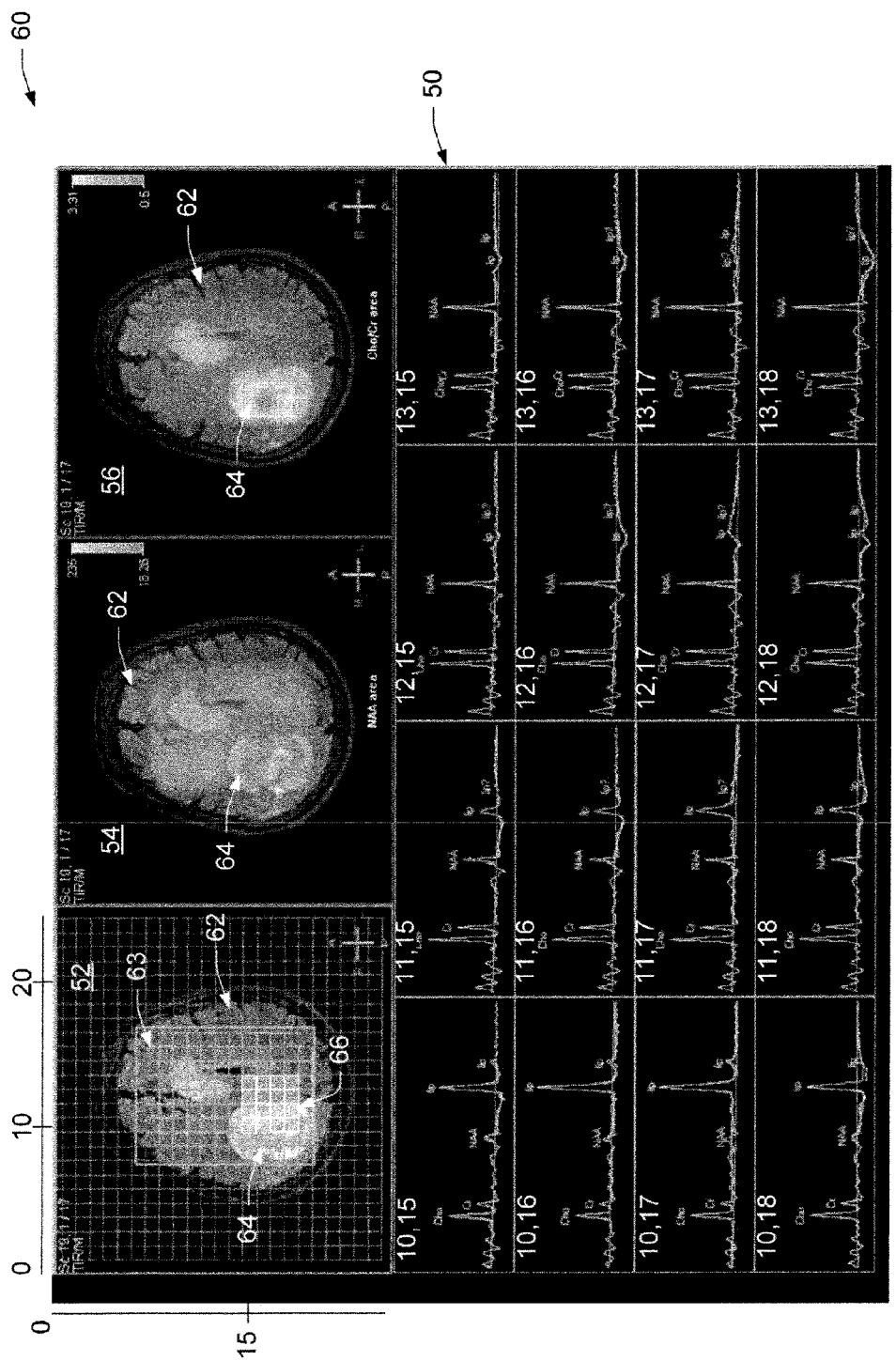
FIG. 2 is a screenshot showing a sample data set generated by applying spectroscopy algorithm(s) to brain tissue to generate a spectrum for each of a plurality of selected voxels.

FIG. 2 is a screenshot 60 showing a sample data set generated by applying the spectroscopy algorithm(s) 28 from brain tissue 62 to generate a proton spectroscopy spectrum 50 for each highlighted voxel, a 4×4 voxel array 66 in the illustration of FIG. 2. Image 52 is an MR image of the human brain with an MR spectroscopy voxel map 63 overlaid on it. For MR image 52 of the brain tissue 62, the corresponding spectra are presented, e.g. on the display 22 (FIG. 1). The brain tissue 62 includes a tumor or lesion 64. A 4×4 subset of voxels 66 overlaying the tumor 64 and the healthy brain tissue 62 is highlighted. The 4×4 subset of voxels extends from row 15 to row 18, and from column 10 to column 13, of the MR image, where rows are numbered from the top and columns from the left.

Chemical composition of the metabolites in each voxel is obtained from each voxel using semi-automated algorithms provided by the MR device. In one embodiment, the MR device is a Philips Achieva MR scanner. According to one example, the chemical composition of each voxel comprises choline (Cho), creatinine (Cr), N-Acetyl Aspartate (NAA), and/or lipid (lip). Chemical compositions of each voxel 66 in the subset are also presented in the screenshot, each being labeled according to its row and column coordinates. For example, voxels in column 10, near the center of the tumor 64, exhibit high amounts of lipid and little or no NAA and creatinine. Voxels in column 11 exhibit higher amounts of NAA and creatinine and lower amounts of lipid, relative to voxels in column 10. Voxels in column 13, overlaying healthy brain tissue 62, exhibit little or no lipid and relatively high amounts of NAA and creatinine. The chemical compositions of each voxel can be used to distinguish between soft tissue types in an MR image and/or displayed for its diagnostic value. Image 54 depicts the MR image overlaid with highlighting indicating relative concentrations of NAA, and image 56 is overlaid with highlighted indicative of relative Cho/Cr ratios. Using the spectral characteristics of each voxel an attenuation value is assigned based upon a dominant characteristic or as a weighted-average. It will be appreciated that the described systems and methods are not limited to distinguishing and assigning attenuation values between brain tissue and tumor tissue, including tumor tissue following radiation or other therapy, but may be employed to distinguish between any types of tissue that exhibit different chemical compositions.

Figure 3:
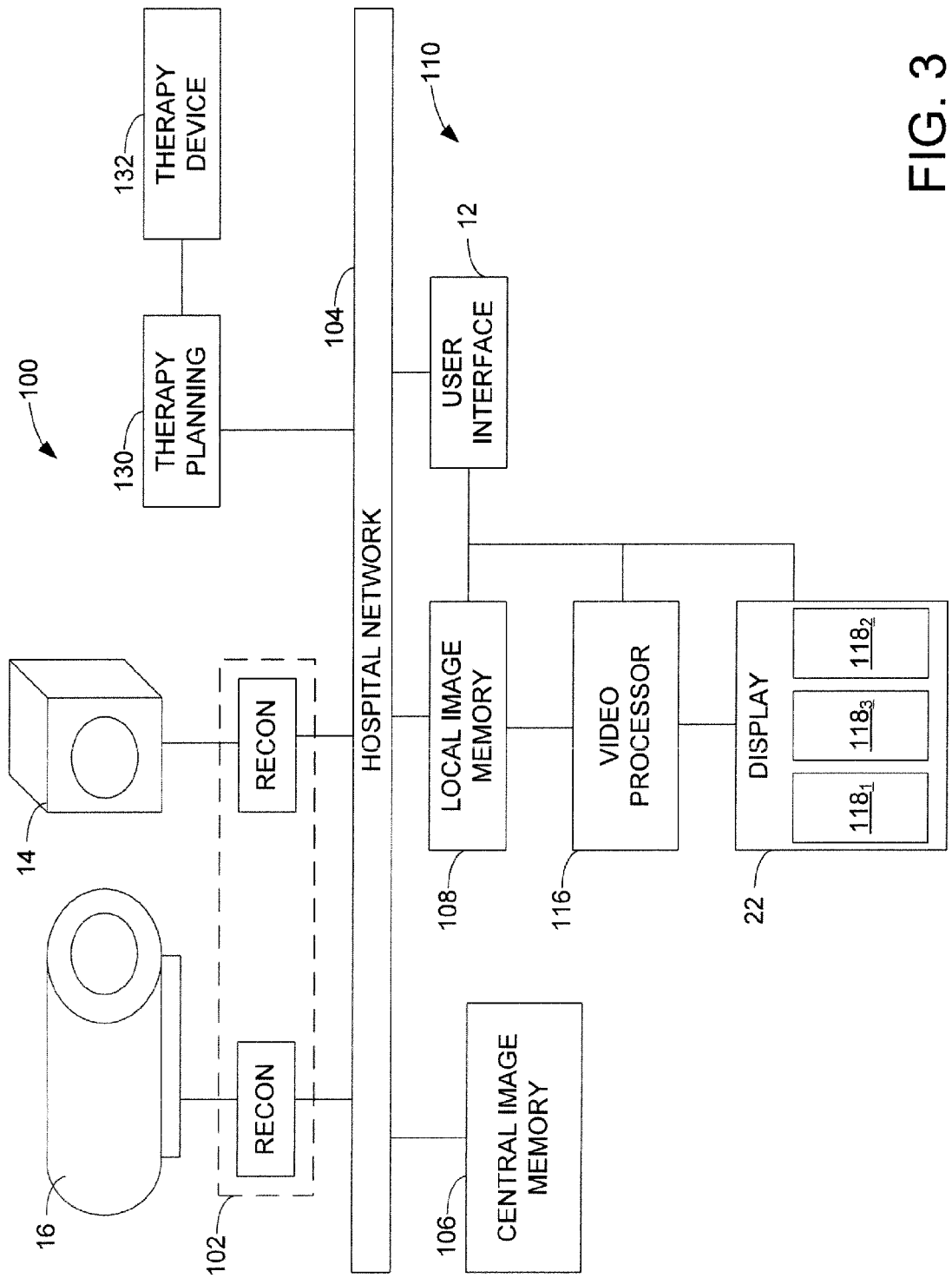
FIG. 3 illustrates an exemplary hospital system that includes a plurality of imaging devices, such as PET, MR, or the like, which generate imaging data that are reconstructed by individual or shared reconstruction processors to generate 3D image representations.

With reference to FIG. 3, an exemplary hospital system 100 may include a plurality of imaging devices, such as PET 14, MR 16, or the like, which generate imaging data that are reconstructed by individual or shared reconstruction processors 102 to generate 3D image representations. The image representations are communicated over a network 104 to a central memory 106 or a local memory 108.

At a station 110 connected with the network, an operator uses user interface 12 to move a selected patient MR image, PET image, spectroscopy information and/or MRAC map to or between the central memory 106 and the local memory 108. A video processor 116 displays an MR image, e.g. a T1 weighted or proton density image, a spectroscopy image, MRAC map corrected PET image, spectra, etc., in various viewports 118. For instance, a PET image (pre- or post-attenuation correction) can be displayed with the MRAC voxel map overlaid thereon in a first viewport $118_1$, of the display 22. The MR image can be displayed in a second viewport $118_2$. A third view port $118_3$ can display an overlay of the MR image and the PET image.

In another embodiment, the MRAC map is overlaid on the PET image displayed in the first viewport $118_1$ and the PET image overlaid with highlighting indicating relative concentrations of a first metabolite (e.g., NAA or the like) is displayed in the second viewport $118_2$. A PET image overlaid with highlighting indicative of relative Cho/Cr ratios is displayed in the third viewport $118_3$. Alternatively, the third viewport (or a fourth viewport, not shown) displays spectral data for all or a subset of the voxels in the PET image or a region thereof.

The corrected PET image, as well as the MR image may be used in other applications. For instance, a therapy planning station 130 can use the corrected PET image and/or other images to plan a therapy session. Once planned to the satisfaction of the operator, the planned therapy can, where appropriate to an automated procedure, be transferred to a therapy device 132 that implements the planned session. Other stations may use the attenuation-corrected PET image in various other planning processes.

In another embodiment, the overlay displayed in viewport $118_3$ is adjustable to weight the MR image relative to the PET image (e.g., the attenuation corrected PET image, the non-attenuation corrected PET image, etc.), or vice versa. For instance a slider bar or knob (not shown), which may be mechanical or presented on the display 22 and manipulated with an input device, may be adjusted to vary the weight of the MR image or the PET image. In one example, an operator can adjust the image in viewport $118_3$ from purely MR data (which may be shown in viewport $118_1$), through multiple and/or continuous combinations of MR and PET image data, to purely PET image data (as is shown in viewport $118_2$). For instance, a ratio of MR image data to PET image data can be discretely or continuously adjusted from 0:1 to 1:0. As another option, the MR image can be displayed in grayscale and the PET image can be colorized. Anatomical landmarks in the MR image help relate the PET image to the subject.

Figure 4:
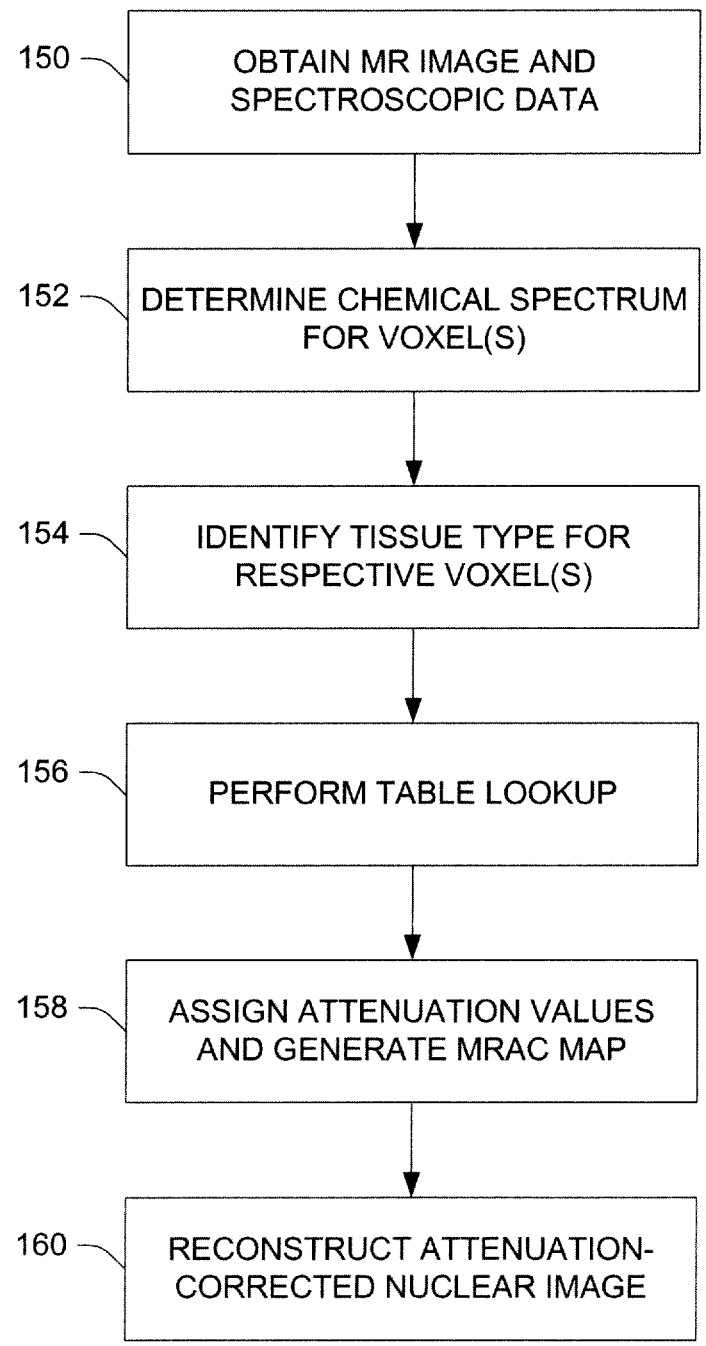
FIG. 4 illustrates a method for correcting attenuation in a nuclear image, in accordance with one or more aspects described herein.

FIG. 4 illustrates a method for correcting attenuation in a nuclear image, in accordance with one or more aspects described herein. At 150, MR image data is obtained for one or more voxels in an MR image, and spectroscopic data for at least one of the one or more voxels in the MR image is obtained. At 152, a chemical spectrum for each of the one or more voxels is determined. At 154, a tissue type for each respective voxel is identified as a function of a chemical composition of the voxel determined from the spectrum of the voxel. For instance, the chemical composition of a given voxel can include one or more of choline, creatinine, N-Acetyl Aspartate, and/or lipid. From the specific chemical composition of a given voxel, the tissue type represented thereby is determined.

At 156, a table lookup is performed to identify attenuation values for respective tissue types. At 158, an attenuation value is assigned to each voxel in the MR image as a function of the tissue type identified for the voxel, to generate an MR attenuation correction (MRAC) map. At 160, an attenuation-corrected nuclear image is reconstructed from acquired nuclear image data using the MRAC map.

Figure 5:
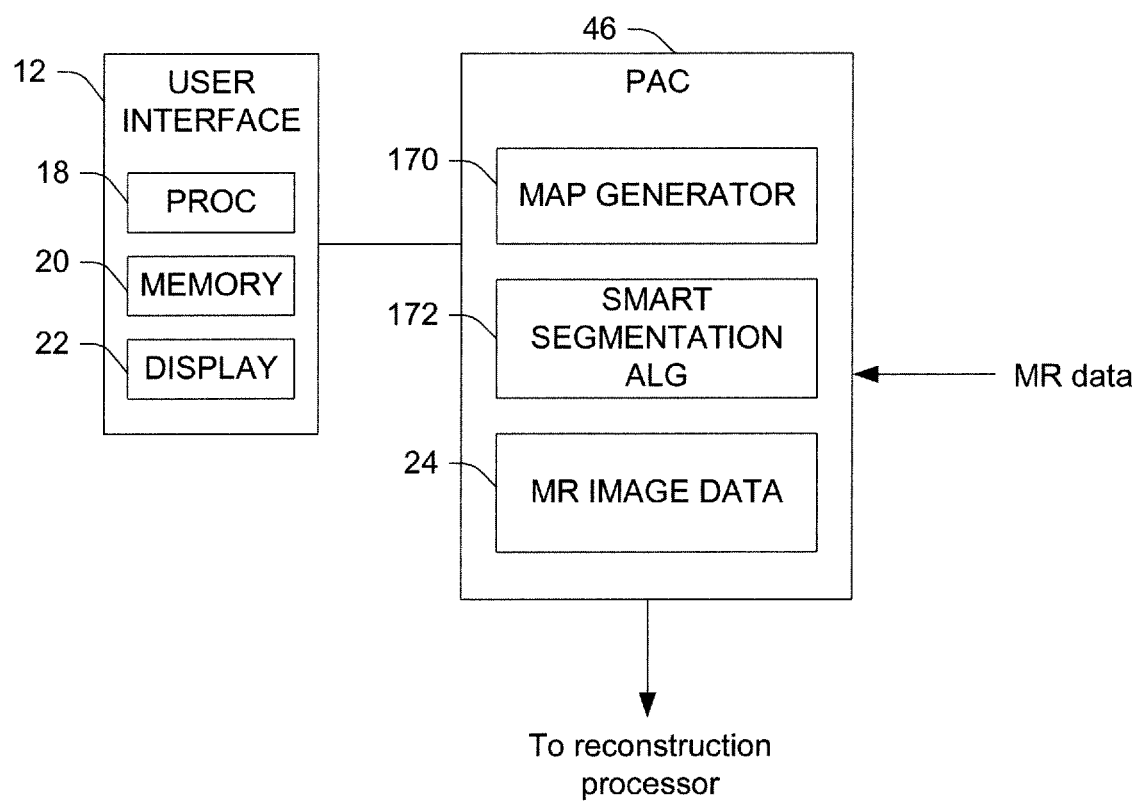
FIG. 5 illustrates the PAC component that generates one or more attenuation correction maps or templates for correcting attenuation in a nuclear image caused by RF coils positioned on or near a patient during a combined nuclear/MR scan (e.g., PET/MR, SPECT/MR, etc.).

FIG. 5 illustrates the PAC component 46 that generates one or more attenuation correction maps or templates for correcting attenuation in a nuclear image caused by RF coils positioned on or near a patient during a combined nuclear/MR scan (e.g., PET/MR, SPECT/MR, etc.). The PAC component facilitates accounting for RF coils or accessories that affect PET image quality (e.g., cause photon attenuation) by analyzing RF coil position relative to a subject being imaged when the coil/accessory does not have a fixed relationship to a subject support tabletop. For instance, certain RF coils and accessories are always in constant strict rigid physical coordinates with respect to particular patient anatomy while imaging (whether PET or MR imaging). Knowledge of the coil position is used to generate templates for attenuation correction of a PET image of the surface RF coils and applied to the PET image based on smart organ segmentation during image reconstruction.

One example of an RF coil that can cause the described attenuation in a PET image is a breast coil. Breast coils are generally rigid structures but are not necessarily located at a fixed position relative to the subject support tabletop. However, the breast coil has a fixed relationship to the anatomy of the subject. This knowledge can be used to infer the breast coil position in (x, y, z) space, i.e., with the same coordinate system as the nuclear data. The described technique is applicable to a subset of RF coils and accessories, which includes but is not limited to: head coils, bilateral breast coils; endorectal coils; shoulder coils; knee/foot/ankle coils; sensitivity encoding (SENSE) versions of these coils (e.g., having 8 elements); breast imaging mattresses; headphones; nurse call devices; etc. Such devices are in, or can be placed in, fixed position relative to certain imagable anatomy, rather than in a fixed position on the tabletop, and attenuation maps for these devices can thus be spatially incorporated into the acquired patient images for correction caused by their attenuation. It will be appreciated that in some cases the local coils may be a combined transmit/receive (T/R) coil, thus the technique is not limited to receive-only coils.

Accordingly, the PAC component 46 includes a map generator 170 that generates one or more coil attenuation correction maps, or templates, that are used during PET image reconstruction for account for attenuation caused by MR coils or accessories in the PET field of view during a PET scan. In one embodiment, the coil attenuation maps are combined with the tissue attenuation correction map 30. In another embodiment, the PET data is corrected using both maps.

A smart segmentation algorithm 172 is executed to detect the presence of certain tissue-types or anatomical features in the MRI images and place (align) the previously determined coil attenuation map for the coil/device in appropriate proper relative location on the patient. According to an example, the segmentation algorithm identifies an outline of the breast, and the aligner aligns the attenuation map for the breast coil to the identified outline. In another example, the segmentation algorithm identifies an outline for a prostate being imaged, and the aligner aligns an attenuation map for an endorectal prostate coil to the identified outline for attenuation correction during reconstruction of the PET image. It will be appreciated that the described technique(s) can be employed in scenarios in which dual-modality PET/MR sequential imaging is used, in which combined PET/MR simultaneous imaging is used, or in any other suitable scenario in which MR coils or other accessories are positioned in a PET field of view during a PET scan.

The PAC component 46 is coupled to the user interface 12, and is controlled by the processor(s) 18. Additionally, information received, generated, and/or manipulated by the PAC component or its subcomponents/algorithms can be stored in the memory 20 and optionally displayed on the display 22. In one embodiment, one or more of the attenuated PET image, the MR image, and the attenuation-corrected PET image are displayed to a user on the display. A user can view the anatomical landmarks or contours identified from the MR image, and, based thereon, can position, or adjust the position of, the coil attenuation map or template in a corresponding position to the patient, and hence the PET image data, for use in reconstructing an attenuation-corrected PET image.

In one embodiment, an initial scout or pilot scan of a patient is performed using an MRI device, image slices are generated, and the smart segmentation algorithm is executed to identify landmarks in the image slices to model the patient anatomy. Once the scout scan data is acquired and the coil position is deduced or inferred from the identified landmarks, the PAC component aligns the pre-generated coil attenuation correction map with the anatomical model.

In another embodiment, the MR imager 16 (FIG. 1) is used to acquire data during a scout scan that is used by the map generator 170 to generate a low-resolution B1 map. For instance, at 3T and above, dielectric effects of the coils or accessories cause distortion in the B1 field. In order to reduce this distortion, multi-channel transmit coils are employed with an RF shim when imaging the patient. Such B1 mapping techniques are being developed to operate in a time-efficient manner and can be used to help characterize the field of the applied coil. A spatially-resolved B1 map is then used to infer coil position relative to the MR scanner, and hence the PET detectors and the patient anatomy. Additionally, the B1 map can be used to estimate coil position with or without anatomical structure (e.g., landmark) information.

In another embodiment, an attenuation-causing coil or device, or portion thereof, is adjusted or aligned to the patient using identified anatomical landmark information, to ensure that the coil or device is properly aligned with the attenuation map therefor. For instance, a nurse-call device (e.g., a device with a button and/or intercom that a patient uses to call a nurse or the like) may be positioned in a patient's hand once the position of the hand has been identified, so that when an attenuation correction map for the call device is aligned to the patient's hand, it is also correctly aligned to the call device. According to another example, all or a portion of a coil is adjusted by a technician or operator to align it to one or more identified anatomical structures, thereby facilitating improved correlation or alignment to a standard pre-generated attenuation correction map. In this manner, non-symmetrical coils or devices can be properly aligned to the patient's anatomy, and thus to the attenuation correction map(s) used to correct for attenuation caused by the coil or device.

Figure 6:
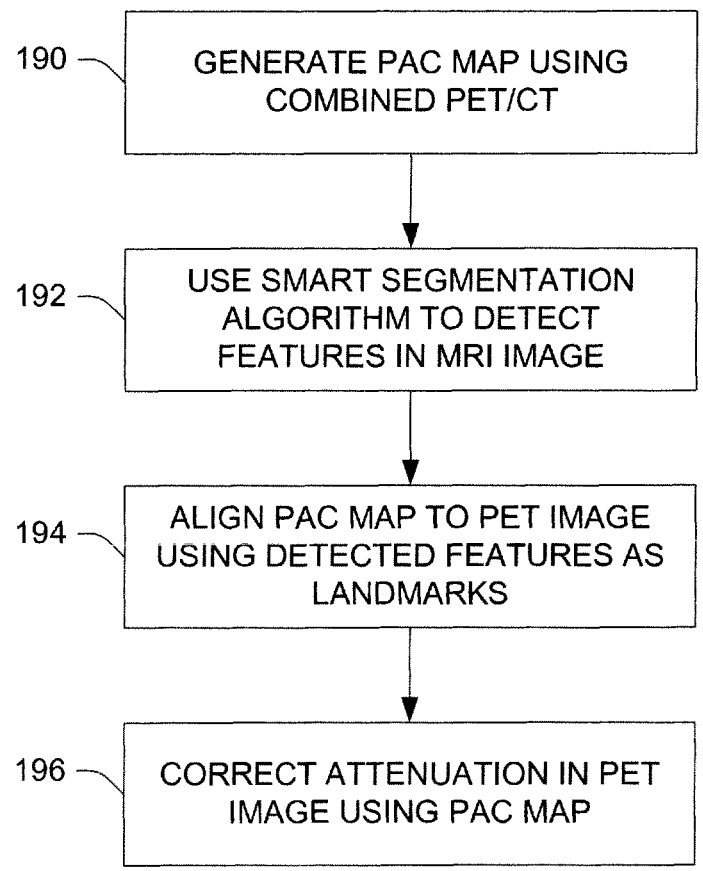
FIG. 6 illustrates a method of correcting for attenuation in a PET image due to MR coils or accessories that are in the PET field of view during a PET scan and that have a fixed location relative to the patient's anatomy.

FIG. 6 illustrates a method of correcting for attenuation in a PET image due to MR coils or accessories that are in the PET field of view during a PET scan and that have a fixed location relative to the patient's anatomy. At 190, a photon attenuation correction (PAC) map (e.g., a coil attenuation map) for each of a plurality of local MR coil types is generated or calibrated and stored in the CAC memory 47. In one embodiment, the PAC map is generated using a CT scanner, other X-ray scanner, radiation attenuation measurements, a combined PET/CT scanner or the like, using known techniques. At 192, a smart segmentation algorithm is executed to detect anatomical features in an MR image of a patient. For instance, a body contour, such as a breast outline, is identified in an MRI image of the patient by the smart segmentation algorithm, and the PAC map is overlaid on the corresponding body contour. That is, using landmarks identified in the MRI image, the map is aligned to corresponding landmarks in PET imaging space, at 194. At 196, the PET image is corrected for coil attenuation using the PAC map.

It will be appreciated that a plurality of PAC maps can be pre-generated for different RF coils and/or accessories, as well as for different patient sizes, to facilitate rapid PAC map selection and alignment for PET image reconstruction with attenuation correction. For instance, a plurality of maps can be generated for obese patients, tall patients, short patients, pediatric patients, etc. Similarly, one or more maps can be generated for each of a variety of RF coils and accessories (e.g., breast coils, head coils, knee coils, headphones, etc.).

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. An image correction system, including:
    a memory that stores magnetic resonance (MR) spectroscopic image data acquired during an MR scan of a subject;
    a processor that:
    distinguishes voxels associated with bone from voxels associated with tissue using MR image data, and excludes bone voxels from spectroscopic analysis;
    determines a spectrum for voxels selected from the MR spectroscopic image data;
    determines a tissue type for each voxel based on its spectrum;
    converts each tissue type into a photon attenuation value; and
    assembles the attenuation values for each voxel into an MR attenuation correction (MRAC) map; and
    a nuclear imaging reconstruction processor that reconstructs nuclear image data into attenuation corrected nuclear image data in accordance with the MRAC map.

2. The system according to claim 1, wherein the processor accesses a lookup table (LUT) including known 511 keV photon attenuation values for a plurality of tissue types, which are assigned to respective voxels in the MRAC map as a function of the tissue type associated with the chemical composition of each voxel.

3. The system according to claim 1, further including:
    at least one of a positron emission tomography (PET) scanner or a single-photon emission computed tomography (SPECT) scanner that generates the nuclear image data.

4. The system according to claim 1, wherein the processor employs the MRAC map to reconstruct an attenuation-corrected nuclear image from the attenuation corrected nuclear image data.

5. The system according to claim 4, further including:
    a display that presents at least one of the attenuation corrected nuclear image, spectra of selected voxels, and chemical composition information.

6. The system according to claim 5, wherein the display presents an adjustable overlay of an MR image and the attenuation corrected nuclear image, the adjustable overlay being adjustable between a ratios of 0:1 and 1:0 of MR image data to nuclear image data.

7. The system according to claim 5, wherein the chemical composition information for each voxel includes one or more of choline, creatinine, N-Acetyl Aspartate, and lipid, and wherein tissue type associated with each voxel is determined as a function of the specific chemical composition thereof.

8. The system according to claim further including:
    an MR imaging device that acquires the MR image data, and a nuclear scanner that acquires the nuclear image data.

9. The system according to claim 8, wherein the MR device generates low-contrast T1-weighted or proton density weighted MR image data of the subject, and wherein the processor analyzes the low-contrast MR image data to distinguish voxels associated with air or air-dominated tissue from voxels associated with other tissue and excludes air or air-dominated tissue voxels from spectroscopic analysis.

10. The system according to claim 9, wherein the MR device generates chemical shift image data and the processor analyzes the chemical shift image data of the subject to distinguish voxels associated with water-dominated tissue from voxels associated with fatty tissue.

11. The system according to claim 1, wherein the nuclear imaging reconstruction processor employs a pre-generated coil attenuation correction map that describes attenuation characteristics of at least one of a local MR coil and an accessory positioned on the subject when reconstructing the nuclear image data.

12. A method of correcting attenuation in a nuclear image, including:
    obtaining MR image data for one or more voxels in an MR image and spectroscopic data for at least one of the one or more voxels in the MR image;
    distinguishing voxels associated with bone from voxels associated with tissue using the MR image data, and excluding bone voxels from spectroscopic analysis;
    determining a chemical spectrum for each of the one or more voxels;
    identifying a tissue type for each respective voxel as a function of a chemical composition of the voxel determined from the spectrum of the voxel;
    performing a table lookup for attenuation values for respective tissue types;
    assigning an attenuation value to each voxel in the MR image as a function of the tissue type identified for the voxel, to generate an MR attenuation correction (MRAC) map; and
    reconstructing an attenuation-corrected nuclear image from acquired nuclear image data using the MRAC map.

13. The method according to claim 12, further including displaying the attenuation corrected nuclear image and spectra of selected voxels to a user.

14. The method according to claim 12, further including: generating low-contrast T1-weighted or proton density weighted MR image data of a subject, distinguishing voxels associated with air or air-dominated tissue from voxels associated with tissue using the low-contrast MR image data, and excluding air voxels from spectroscopic analysis.

15. The method according to claim 12, further including: generating chemical shift image data of a subject and distinguishing voxels associated with water-dominated tissue from voxels associated with fatty tissue.

16. The method according to claim 12, wherein the nuclear image data is acquired using at least one of a positron emission tomography (PET) imaging technique or a single-photon emission computed tomography (SPECT) imaging technique.

17. The method according to claim 12, wherein the attenuation values include 511 keV photon attenuation values for a plurality of tissue types.

18. The method according to claim 12, further including: employing a pre-generated coil attenuation map that describes attenuation characteristics of at least one of a local MR coil and an accessory positioned on or in a subject, when reconstructing the attenuation corrected nuclear image (37).

19. An anatomical image system including a processor programmed to perform the method according to claim 12.

20. The method of claim 12, further including: planning a therapy session for the subject using the attenuation-corrected nuclear image, and exporting a planned therapy to a therapy device for automated execution.

21. A computer readable medium having stored thereon software for controlling one or more computers to correct for attenuation in a nuclear image, the software including instructions for controlling one or more processors to perform the method according to claim 12.

22. An apparatus for correcting attenuation in a nuclear image using magnetic resonance (MR) image data and spectroscopic data, including a processor configured to:
generate MR image data for one or more voxels in an MR image and spectroscopic data for at least one of the one or more voxels in the MR image;
distinguish voxels associated with bone from voxels associated with tissue using the MR image data, and exclude bone voxels from spectroscopic analysis;
determine a chemical spectrum for each of the one or more voxels;
identify a tissue type for each respective voxel as a function of a chemical composition of the voxel determined from the spectrum of the voxel;
perform a table lookup for attenuation values for respective tissue types;
assign an attenuation value to each voxel in the MR image as a function of the tissue type identified for the voxel, to generate an MR attenuation correction (MRAC) map; and
reconstruct an attenuation-corrected nuclear image from acquired nuclear image data using the MRAC map.

23. A method of correcting attenuation in a nuclear image, including:
obtaining MR image data for one or more voxels in an MR image and spectroscopic data for at least one of the one or more voxels in the MR image;
distinguishing voxels associated with bone from voxels associated with tissue using the MR image data, and excluding bone voxels from spectroscopic analysis;
determining a chemical spectrum for each of the at least one of the one or more voxels;
identifying a tissue type for each respective voxel as a function of a chemical composition of the voxel determined from the spectrum of the voxel, wherein the chemical composition of a voxel includes one or more of choline, creatinine, N-Acetyl Aspartate, and lipid, and wherein tissue type associated with each voxel is determined as a function of the specific chemical composition thereof;
performing a table lookup for attenuation values for respective tissue types;
assigning an attenuation value to each voxel in the MR image as a function of the tissue type identified for the voxel, to generate an MR attenuation correction (MRAC) map; and
reconstructing an attenuation-corrected nuclear image from acquired nuclear image data using the MRAC map.

* * * * *